United States Patent [19]

Haaseth et al.

[11] Patent Number: 5,326,751
[45] Date of Patent: Jul. 5, 1994

[54] ENKEPHALIN ANALOGS

[75] Inventors: Ronald C. Haaseth; Victor J. Hruby, both of Tucson, Ariz.

[73] Assignee: Arizona Board of Regents on behalf of the University of Arizona, Tucson, Ariz.

[21] Appl. No.: 904,425

[22] Filed: Jun. 26, 1992

[51] Int. Cl.$^5$ .................. A61K 37/02; C07K 5/12; C07K 7/06
[52] U.S. Cl. .................................. 514/17; 514/9; 514/11; 530/317; 530/330
[58] Field of Search .................. 514/11, 17; 530/330, 530/317, 302

[56] References Cited

U.S. PATENT DOCUMENTS

| | | | |
|---|---|---|---|
| 4,518,711 | 5/1985 | Hruby et al. | 514/11 |
| 4,684,620 | 9/1987 | Hruby et al. | 514/14 |
| 5,061,691 | 10/1991 | Yagi et al. | 530/329 |

OTHER PUBLICATIONS

Toth, G. et al., "[D-Pen$^2$, D-Pen$^5$]enkephalin Analogues With Increased Affinity and Selectivity for Opioid Receptors," J. Med. Chem. 33:249–253 (1990).
Hruby, V. J. and C. A. Gehrig, "Recent Developments in the Design of Receptor Specific Opioid Peptides," Medicinal Research Reviews 9:3:343–401 (1989).
Clark, J. A., et al., "[D-Pen$^2$, D-Pen$^5$]enkephalin (DPDPE): A δ-selective Enkephalin with Low Affinity for μ1 Opiate Binding Sites," E. J. Pharm. 128:303–304 (1986).
Haaseth, R. C. et al., "Potent and Selective 3-position Analogs of DPDPE," INRC/CPDD Meeting Jun. 20–27, 1992 (Poster presented Jun. 27).
Misika, A. et al., "Computer Modeling of Opioid Selective Ligands: Possible New Topographical Relationships to Bioactivity are Examined with New Analogs Designed for δ Opioid Receptor," Peptides (J. Smith and J. Rivier Eds., Escom. 1991).

Primary Examiner—Merrell C. Cashion, Jr.
Assistant Examiner—S. G. Marshall
Attorney, Agent, or Firm—Quarles & Brady

[57] ABSTRACT

A new class of opioid receptor analogs is described based on an alanine substitution in the three position in the enkephalin analog DPDPE. The alanine-substituted analogs show increased selectivity for the delta type of opioid receptors over the mu type of receptors.

17 Claims, No Drawings

ENKEPHALIN ANALOGS

FIELD OF THE INVENTION

The present invention relates to synthetic analogs for enkephalins having unusual opiate receptor binding characteristics.

BACKGROUND OF THE INVENTION

Opioid analgesics are narcotic drugs used for treating a wide variety of clinical symptoms, most particularly pain. The serious drawbacks in the use of plant opioids, such as morphine, including addiction and intestinal blockage, are well known. A form of naturally occurring opiates is found in the nervous tissues of animals. These natural animal opiates are known as enkephalins. Naturally occurring enkephalins, which are part of a larger family of chemical signals known as endorphins, are mixtures of two pentapeptides. Much research effort has been focussed on enkephalins and their analogs in search of analgesics with lesser drawbacks.

As a part of this research, the receptors to which opioids bind have been studied and characterized. The opioid receptors are the molecules on the cell surface which recognize the opioid and imitates its biological effects. The opioid receptors have been found to vary in their characteristics, and several types or classes of such receptors have been identified. The major types of proposed receptors are the mu, delta, and kappa receptors. All three receptors are involved in analgesia, but differ in other pharmacological effects. The mu receptors are associated with respiratory depression and inhibition of gastrointestinal transit. Kappa receptors mediate sedation. The delta receptors also mediate analgesfa, but do not seem to be associated with inhibition of gastrointestinal transit. Some recent evidence suggests that compounds selective for the delta receptors may not be subject to the dependence and tolerance problems generally associated with opiate analgesics that are non-selective as to receptor type or are selective for the mu receptor. Opioid compounds which bind to the opiate receptors are said to be "agonists" if they inhibit electrically stimulated output of neurotransmitters in tissues containing receptors and "antagonists" if they prevent such inhibition. Morphine is an agonist and naloxone is an antagonist.

The natural enkephalins, as stated, are a mixture of two pentapeptides, methionine enkephalin (H-Tyr-Gly-Gly-Phe-Met-OH) and leucine enkephalin (H-Tyr-Gly-Gly-Phe-Leu-OH). Much research has been directed toward identifying analogs of these compounds which are selective as to the types of opiate receptors to which they bind. See, e.g., Hruby and Gehrig, *Medicinal Research Reviews*, Vol. 9, No. 3, pp. 343-401 (1989).

One class of analogs of natural enkephalins has been identified with relatively high selectivity for delta-type opiate receptors. This type is based on substitutions for the second and fifth amino acid residues of the pentapeptides, with either cysteine or with D- or L-penicillamine (beta, beta-dimethylcysteine). A particularly noteworthy member of that class is [D-Pen$^2$, D-Pen$^5$] enkephalin, or "DPDPE," which has the D-Pen residues at the second and fifth positions joined by a disulfide link to make a cyclic molecule. This compound, and several analogs of it, are described in U.S. Pat. No. 4,518,711. The selectivity of DPDPE for the delta receptor is also described in Clark et al., *Eur. Jour. Pharm.*, 128, pp. 303-304 (1986) among others. In addition, analogs of DPDPE have also been created, principally consisting of variations at the fourth residue (Phe), some of which have an even greater selectivity for the delta receptor. However, compounds of even greater selectivity for the delta receptors would still be useful, not only as candidates for clinical application, but also as research tools to further characterize the functioning of these biologically significant receptors.

SUMMARY OF THE INVENTION

The present invention is summarized in that a novel class of enkephalin analogs is described, some members of which have enhanced selectivity for the delta opiate receptors, which are generally characterized by a substitution of an alanine amino acid residue at the third position for the glycine residue in DPDPE. The substitution is generally designated DPADPE.

The new class of enkephalin analogs described here includes members which have the highest selectivity for the delta opiate receptors yet identified. In particular, halogen substitutions to the fourth residue (Phe) result in additional selectivity as previously reported for DPDPE analogs by Toth et al., *J. Med. Chem.* 33, pp. 249-253 (1989).

The present invention is also characterized as a process for inducing analgesia in animals by administration of a safe and effective amount of an opiate delta receptor agonist which is a member of this novel class of compounds.

The general group of polypeptides described here can be characterized by the formula:

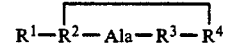

wherein
- R$^1$ is L-tyrosine or halogen or methyl substituted L-tyrosine;
- R$^2$ is D-penicillamine or D-cysteine;
- R$^3$ is phenylalanine or phenylalanine with one to three of the same or different halogen, methyl, nitro, or lower alkyl substitutions; and
- R$^4$ is D-penicillamine, L-penicillamine, D-cysteine or L-cysteine.

These compounds are generally agonists for the delta receptor, and members of this class have very high selectivity for the delta over the mu receptors.

The preferred group of compounds of the present invention are polypeptides of the formula:

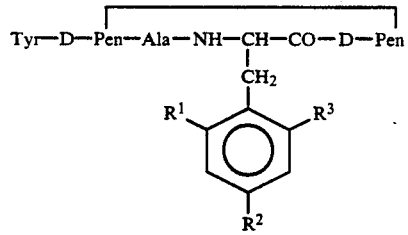

wherein R$^1$, R$^2$ and R$^3$ are the same or different and are H, F, Cl, Br, I, NO$_2$, NH$_2$ or a lower alkyl of less than five carbons.

Other objects, advantages and features of the present invention will become apparent from the following detailed description of the invention.

DETAILED DESCRIPTION OF THE INVENTION

As noted above, the development of receptor-specific compounds which, as a class, exhibit a range of receptor specificities and affinities, is desirable for both research and clinical applications. The applicants herein disclose conformationally stable DPDPE analogs which, while maintaining delta receptor specificity, exhibit a range of receptor-binding properties. DPDPE has the following formula:

$$H-Tyr^1-D-Pen^2-Gly^3-Phe^4-D-Pen^5-OH$$

Each DPDPE analog disclosed herein is substituted in the third aminoacyl residue by an alanine substitution for Gly$^3$.

Before proceeding further, it is necessary to explain briefly the terminology used to describe polypeptides. Peptides are identified by amino acid sequence using established abbreviations. For example, as used herein, "Gly" stands for glycine, "Tyr" stands for tyrosine, "Pen" stands for penicillamine, "Cys" stands for cysteine, and "Phe" stands for phenylalanine. Polypeptide derivatives in which one or more of the amino acids has been replaced by another amino acid are often described by reference to the basic compound and the position and nature of the substitution. The position of substitution is usually identified by referring to the number of the amino acid in the sequence, starting with the amino acid at the amino terminus of the peptide chain. For example, H-Tyr-Gly-Gly-Phe-Pen-OH is written as ([Pen$^5$]-enkephalin) signifying that penicillamine has been substituted for the leucine or methionine normally forming the fifth amino acid from the amino terminus in enkephalin. Additionally, amino acids may exist as stereoisomers in either L or D configurations. The L configuration is presumed here unless D is stated. Furthermore, the five amino acids that form the prototype enkephalin molecule are numbered one through five with numbers increasing from the amino to the carboxy end of the peptide. However, it is not beyond the scope of this invention for additional amino acids to be linked to the pentapeptide at one or more positions. In such case, reference is made to substitutions and modifications of the five prototypical positions. As used here, halogens are meant to describe fluorine (F), Chlorine (Cl), Bromine (Br), and Iodine (I). Lower alkyls are alkyl compounds of less than five carbons.

In place of the Gly$^3$ of DPDPE, the class of analogs disclosed herein are broadly characterized as L-Ala$^3$-DPDPE analogs. Several of the L-Ala$^3$-DPDPE analogs exhibit even stronger selectivity for delta-type opioid receptors than do the unsubstituted DPDPE's. In contrast, DPDPE substituted in the third aminoacyl position with Ser$^3$ do not show significant biological specificity for such receptors. A [Ser$^3$] DPDPE analog tested in a binding potency assay did not demonstrate a high binding potency at delta receptors. See Misicka, A, et al., *Peptides* 140–141 (1991). L-Ala$^3$-substituted DPDPE is sometimes referred to here as DPADPE.

This class of analogs can be broadly characterized as follows:

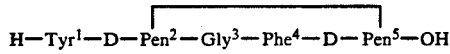

wherein
R$^1$ is L-tyrosine, or halogen or methyl substituted L-tyrosine;
R$^2$ is D-penicillamine or D-cysteine;
R$^3$ is phenylalanine or phenylalanine with one to three of the same or different halogen, methyl, nitrate, or lower alkyl substitutions; and
R$^4$ is D-penicillamine, L-penicillamine, D-cysteine or L-cysteine.

The preferred class of DPADPE analogs is characterized by the formula:

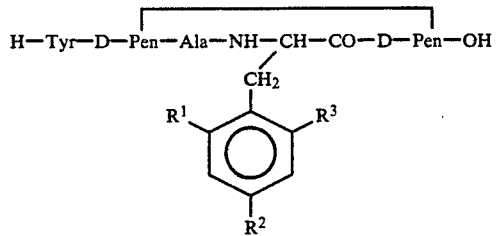

wherein R$^1$, R$^2$ and R$^3$ are the same or different and are H, F, Cl, Br, I, NO$_2$, NH$_2$ or a lower alkyl of less than five carbons.

Analogs of DPADPE are also reported. These analogs, which incorporate substituted Phe$^4$ residues for Phe$^4$-DPADPE, demonstrate a preference for, and a range of specificities for, delta receptors.

Additional L-Ala$^3$-substituted DPDPE analogs within the scope of the present invention are also envisioned. It may be that modifications to the amino acid at the amino end of DPADPE could include the addition of an acetyl group, a phenylalanine residue, or a small peptide to its amino-terminal end. Similarly, substitutions at Tyr$^1$ and additional Phe$^4$ substitutions, known to affect receptor specificity in other enkephalin analogs, are envisioned within the group described above. Furthermore, substitutions of D-Cys for D-Pen at position 2, and/or L- or D-Cys for D-Pen at position 5 would maintain the cyclic structure of DPADPE, and would likely confer a high level of specificity for delta receptors in the fashion of DPDPE and DPADPE.

All of the above such modifications would likely retain significant opioid-receptor specificity since it appears that specificity persists if a phenol ring and a free amino group remains in the first amino acid position of the enkephalin-like pentapeptide. Any or all of the envisioned substitutions could prove necessary to decrease the cost of their manufacture for commercial purposes, or to associate the enkephalin function with other desired physiological functions, or to enhance the thermostability of compounds within the class of Ala$^3$-substituted enkephalin analogs.

The compounds of the present invention were examined for their ability to inhibit electrically induced muscle contractions in the guinea pig ileum (GPI) and in the mouse vas deferens (MVD) assay systems. Agonists of opioid receptors, such as the DPDPE analogs herein disclosed, mediate inhibition of muscle contraction. The GPI preparation has been shown to contain primarily mu-type opiate receptors, with some kappa-type. The MVD preparation contains primarily delta-type opiate receptors, with some kappa and mu receptors. These assays measure the nanomolar concentration at which electrically stimulated contractions are 50% inhibited ($IC_{50}$) in MVD and GPI tissues. Thus, comparisons of $IC_{50}$ values in these two tissues, as shown in Table I, indicate the receptor specificity of the tested analogs. Compounds of the present invention showed a higher activity in the MVD assay that in the GPI assay, thereby confirming their specificity for the delta receptor.

The binding potencies of each compound for mu and delta receptors in rat brain extracts was determined by competition assays against radiolabelled compounds known to bind opioid receptors. [$^3H$]CTOP is a ligand that is highly selective for mu-type opioid receptors. [$^3H$][p-Cl-Phe$^4$]DPDPE is known to be a highly selective ligand for delta-type opioid receptors. [$^3H$]CTOP and [$^3H$][p-Cl-Phe$^4$]DPDPE are both commercially available. The ability of a tested compound to displace tritiated ligands from their respective receptor molecules is a measure of the compound's binding potency for the receptor of the displaced ligand. These assays measure the nanomolar concentration at which radiolabelled material is 50% displaced ($IC_{50}$). Thus, comparisons of $IC_{50}$ values in these two tissues, as shogun in Tables II, indicate the relative potency with which each analog is associated with the mu and delta opioid receptors of the brain. The results shown in Table 2 indicate that the cyclic enkephalin analogs herein disclosed exhibit weak binding to mu receptors as determined by minimal displacement of [$^3H$]CTOP. Instead, these cyclic enkephalin analogs, demonstrate higher affinity for delta receptors as measured by displacement of [$^3H$][p-Cl-Phe$^4$]DPDPE. The selectivity of one analog, [p-F-Phe$^4$]DPADPE, for delta receptors in the brain is among the highest ever measured for a synthetic peptide.

The enhanced specificity of certain tested compounds for delta-type opioid receptors is also demonstrated in the ratio coles of Tables I and II. The ratios in table I relate each compound's preference for mu receptors to its preference for delta receptors. In Table II, the ratios compare biological activity in competitive binding assays to receptor-containing brain tissue. Note that the compounds DPADPE, and DPADPE with chlorine and bromine substitutions at the Phe$^4$, all demonstrate significantly higher binding potencies and selective biological activity for delta receptors as compared to the DPDPE standard. Other DPADPE analogs, e.g. the fluorine, iodine, and nitro substitutions to Phe$^4$, all display comparable or slightly enhanced potency and bioactivity relative to DPDPE.

TABLE 1

| COMPOUND | $IC_{50}(nM) \pm$ GPI | S.E.E.[1] MVD | RATIO ($\mu/\delta$) |
|---|---|---|---|
| [L—Ala$^3$]DPDPE (DPADPE) | 121417 ± 81387 | 11.77 ± 1.62 | 10,315 |
| [D—Ala$^3$]DPDPE | 33285 ± 817 | 572 ± 131 | 58.2 |
| [L—Ser$^3$]DPDPE | 39427 ± 7159 | 251.9 ± 32.5 | 156 |
| [D—Ser$^3$]DPDPE | 3% inh at 100 mM | 1279 ± 245 | >79 |
| [L—Abu$^3$]DPDPE | 4869 ± 345 | 84.9 ± 12.5 | 57 |
| [D—Abu$^3$]DPDPE | 29909 ± 2673 | 1952 ± 204 | 15 |
| [AC$_5$C$^3$]DPDPE | 857 ± 31.7 | 369.9 ± 162.4 | 2.3 |
| [p-F—Phe$^4$]DPADPE | 4604 ± 1011 | 3.606 ± 0.367 | 1,276 |
| [p-Cl—Phe$^4$]DPADPE | 25523 ± 10306 | 1.944 ± 0.295 | 13,129 |
| [p-Br—Phe$^4$]DPADPE | 40821 ± 2952 | 2.953 ± 0.686 | 13,823 |
| [p-I—Phe$^4$]DPADPE | 30764 ± 1553 | 10.95 ± 1.23 | 2,809 |
| [p-NO$_2$—Phe$^4$]DPADPE | 13451 ± 1209 | 3.739 ± 0.356 | 3,597 |
| DPDPE | 11600 | 5.81 | 2,000 |

[1]S.E.E. = Standard error of the estimate.

TABLE 2

| COMPOUND | $IC_{50}(nM) \pm$ [$^3H$] CTOP | S.E.E.[1] [$^3H$] p-Cl—DPDPE | RATIO ($\mu/\delta$) |
|---|---|---|---|
| [L—Ala$^3$]DPDPE (DPADPE) | 10998 ± 13 | 18.4 ± 0.43 | 598 |
| [D—Ala$^3$]DPDPE | >35000 | 535 ± 58 | >65 |
| [L—Ser$^3$]DPDPE | >22523 | 42 ± 3 | >536 |
| [D—Ser$^3$]DPDPE | >50000 | 764 ± 106 | >65 |
| [L—Abu$^3$]DPDPE | 11982 ± 938 | 66.3 ± 30.4 | 181 |
| [D—Abu$^3$]DPDPE | >50000 | 3378 ± 1073 | >14.8 |
| [AC$_5$C$^3$]DPDPE | 1763 ± 45 | 312 ± 39 | 5.6 |
| [p-F—Phe$^4$]DPADPE | 1459 ± 253 | 0.55 ± 0.14 | 2653 |
| [p-Cl—Phe$^4$]DPADPE | 1120 ± 260 | 3.7 ± 0.9 | 303 |
| [p-Br—Phe$^4$]DPADPE | 2708 ± 453 | 5.3 ± 0.86 | 511 |
| [p-I—Phe$^4$]DPADPE | 3668 ± 396 | 12.5 ± 0.5 | 293 |
| [p-NO$_2$—Phe$^4$]DPADPE | 712 ± 3 | 3.5 ± 0.25 | 203 |
| DPDPE | 609 | 5.25 | 116 |

[1]S.E.E. = Standard error of the estimate.

In view of the positive results obtained with these tests, the claimed delta receptor against compounds are believed to be useful candidates for the treatment of pain without the undesirable side effects associated with previously known opiates. Compounds within the scope of the present invention having antagonistic activity are believed to behave in a manner similar to naloxone and, thereby, are believed to be useful in those areas where narcotic antagonists have been useful in the prior art, including the treatment of Alzheimer's disease. See generally, Reisberg, B. et al., 308 N.E.J.M. 721–722 (1983).

Preparation of compounds within the scope of the present invention, and detailed descriptions of the assays used to measure receptor specificity appear in the following examples.

EXAMPLE 1

Preparation of
L-Tyrosyl-S-p-methylbenzyl-D-penicillaminyl-L-alany-L-phenylalanyl-S-p-methylbenzyl-D-penicillaminyl-resin The non-cyclic precursor of DPADPE was prepared using the solid phase synthesis procedures similar to those Hruby et al., *J. Med. Chem.*, 34:pp 1823-1830 (1991). First, Boc-D-Pen(S-p-MeBzl), the carboxy-terminal Boc-amino acid residue of DPADPE, was attached by ester linkage to a solid phase support resin using the method of Gisin, *Helv. Chim. Acta* 56, 1476 (1973). The solid phase support resin was chloromethylated polystyrene (0.6-0.8 mmoles Cl/g resin) cross-linked with 1% divinylbenzene (Peptides International, Louisville, Ky.). 2.00 g of dry Boc-D-Pen(S-p-MeBzl)-resin, substituted to the extent of 0.47 mmoles amino acid/g resin was placed into a solid phase synthesis reaction vessel.

Next, the desired $N^\delta$ Boc-amino acid residues (Boc-L-Phe-OH, Boc-L-Ala-OH, Boc-D-Pen(S-p-MeBzl)-OH, and Boc-L-Tyr-OH) were incorporated sequentially onto the nascent peptide-resin, to yield $N^\delta$ Boc-L-Tyrosyl-S-p-methylbenzyl-D-penicillaminyl-L-alanyl-L-phenylalaninyl-S-p-methylbenzyl-D-penicillaminyl-resin, according to the protocol listed in Agenda A.

AGENDA A

1. Washed peptide-resin for 2 min. with $CH_2Cl_2$ (repeated four times).
2. Treated peptide-resin with trifluoroacetic acid [TFA]:$CH_2Cl_2$:anisole (50:48:2, v/v) for 2 min.
3. Treated peptide-resin as in step 2 for 20 min.
4. Washed peptide-resin for 2 min. with $CH_2Cl_2$ (repeated 3 times).
5. Treated peptide-resin with diisopropylethylamine [DIEA]:$CH_2Cl_2$ (10:90, v/v) for 2 min. (repeated 2 times)
6. Washed for 2 min. with $CH_2Cl_2$ (repeated 4 times)
7. Performed ninhydrin test (Kaiser, et al, *Anal. Biochem.* 34, 595 (1970)). If ninhydrin test was positive, proceeded to step 8; if test was negative, repeated steps 3-7.
8. Treated peptide-resin with 3 equivalents of the next $N^\delta$ Boc-amino acid to be added. $N^{\delta\alpha}$ Boc-amino acids were dissolved in $CH_2Cl_2$ or dimethylformamide [DMF]. If the Boc-amino acid was dissolved in $CH_2Cl_2$, 2.4 equivalents of diisopropylcarbodiimide [DIC] were also added. If the Boc-amino acid was dissolved in DMF, 2.4 equivalents of 1-hydroxybenzo-triazole [HOBt] was added along with 2.4 equivalents of DIC. Reaction proceeded 2-4 hours.
9. Washed for 2 min. with $CH_2Cl_2$ (repeated 4 times)
10. Performed ninhydrin test, as in step 7. If coupling was incomplete, repeated steps 8-10.

EXAMPLE 2

Preparation of
L-Tyrosyl-D-penicillaminyl-L--alanyl-L-phenylalanyl-D-penicillaminyl cyclic (2-5) disulfide 2.8 g of the protected peptide-resin from Example 1 were reacted with 25 mL anhydrous hydrofluoric acid (HF), 1.4 mL p-cresol, and 1.4 mL p-thiocresol at 0° C. for 1 hr to yield a mixture of free peptide and resin. The mixture was evaporated in vacuo, then washed 3 times with 75 mL portions of anhydrous ethyl ether. Four extractions with 25 mL portions of glacial acetic acid [HOAc] removed the resin from the mixture. The peptide-containing fractions of the acetic acid extractions were combined and lyophilized to a white powder which contained the free disulfhydryl form of the pentapeptide [DPADPE(SH)$_2$].

The white powder was dissolved in a minimum amount of 25% methanol/25% acetonitrile/50% water, then purified by HPLC. The HPLC system included a 50 mm (id)×10 cm precolumn hand-packed with Impaq RG1020 PQC-18 bonded silica (20μm particle size and 100° pore size) (Varex Corporation, Burtonsville, Md.), and a Vydac C-18 218TP1520, 50 mm (id)×25 cm column (15-20 μm particle size and 300° pore size). A gradient of 25% to 65% in the organic component was utilized with a solvent system of 0.1% TFA in $H_2O$/$CH_3CN$.

After HPLC purification, the partially purified DPADPE(SH)$_2$ was obtained as a fluffy white powder weighing about 525 mg. The 525 mg of DPADPE(SH)$_2$ was dissolved in 100 ml of 50% methanol/50% water, and argon was bubbled into this solution for 20 min. The solution pH was adjusted to 8.5 with 3N $NH_4OH$, then transferred to an addition funnel, where the argon gas was quickly bubbled into the solution again.

This solution was then added over a period of four hours to a solution of 500 mL water, 250 mL acetonitrile ($CH_3CN$), 250 mL methanol, and 150 mL 0.1M $K_3Fe(CN)_6$. The peptide/$K_3Fe(CN)_6$ solution was stirred for an additional four hours. The pH was then lowered to 4 with HOAc. Thirty mL (settled volume) of Amberlite IRA68 (Sigma Chemical Co., St. Louis, Mo.) converted to the chloride form with 0.1N HCl was added and the solution was stirred for 20 min. The mixture was then filtered, the anion exchange resin was washed with 50 mL of 30% HOAc, and the solution volume was reduced to ca. 200 mL by rotary evaporation. The solution was lyophilized to a yellowish solid, then purified by HPLC as described above, using a gradient of 20% to 60% $CH_3CN$.

HPLC yielded two fractions that contained L-Tyrosyl-D-penicillaminyl-L-alanyl-L-phenylalanyl-D-penicillinaminyl, i.e. DPADPE, H-Tyr-D-Pen-Ala-Phe-D-Pen-OH. The first fraction weighed 280 mg and contained DPADPE of >99% purity. The second fraction weighed 100 mg and contained DPADPE of >85% purity.

Amino acid analysis of the >99%-pure material showed its composition to be Tyr (0.67), Ala (1.11), Phe (1.00) (TLC R$_f$: 0.66 (BAW), 0.72 (BPAW), 0.52 (PrAMW), 0.46 (ACE). The following abbreviations for solvent systems are used above: BAW refers to 1-butanol:acetic acid:water (4:1:1); BPAW refers to 1-butanol:pyridine:acetic acid:water (13:12:2:10); PrAMW refers to 2-propanol:ammonia:water (3:1:1); and AcE refers to acetic acid:ethyl acetate (1:2).

EXAMPLE 3

Preparation of [p-F-Phe$^4$]DPADPE

[p-F-Phe$^4$]DPADPE was prepared as set forth in Examples 1 and 2, except that Boc-L-p-F-Phe-OH was incorporated into the peptide chain instead of Boc-L-Phe-OH in Example 1.

EXAMPLE 4

Preparation of [p-Cl-Phe⁴]DPADPE

[p-Cl-Phe⁴]DPADPE was prepared as set forth in Examples 1 and 2, except that Boc-L-p-Cl-Phe-OH was incorporated into the peptide chain instead of Boc-L-Phe-OH in Example 1.

EXAMPLE 5

Preparation of [p-Br-Phe⁴]DPADPE

[p-Br-Phe⁴]DPADPE was prepared as set forth in Examples 1 and 2, except that Boc-L-p-Br-Phe-OH was incorporated into the peptide chain instead of Boc-L-Phe-OH in Example 1.

EXAMPLE 6

Preparation of [p-I-Phe⁴]DPADPE

[p-I-Phe⁴]DPADPE was prepared as set forth in Examples 1 and 2, except that Boc-L-p-I-Phe-OH was incorporated into the peptide chain instead of Boc-L-Phe-OH in Example 1.

EXAMPLE 7

Preparation of [p-NO₂-Phe⁴]DPADPE

[p-NO₂-Phe⁴]DPADPE was prepared as set forth in Examples 1 and 2, except that Boc-L-p-NO₂-Phe-OH was incorporated into the peptide chain instead of Boc-L-Phe-OH in Example 1.

EXAMPLE 8

Preparation of DPDPE

DPDPE was prepared as set forth in Examples 1 and 2 except that Boc-L-Gly-OH was incorporated into the peptide chain instead of Boc-L-Ala-OH in Example 1.

EXAMPLE 9

Testing receptor specificity in in vitro bioassays

The guinea pig ileum longitudinal muscle-myenteric plexus preparation was prepared following the method of Kosterlitz, et al. *Brit. J. Pharmacol.*, 39, 398–413 (1970). Agonists were added to the tissue bath and remained in contact with the tissue for a maximum of three minutes.

The mouse vas deferens was prepared following the method of Hughes, et al. cites *Brit. J. Pharmacol.*, 53, 371–381 (1975). One pair of vasa deferentia was used in each experiment. The buffer did not contain $Mg^{+2}$ ions and a similar dose cycle was used as in the GPI assay.

EXAMPLE 10

Testing Bioactivity of claimed compounds by Inhibition of Opiate Receptor Binding in Rat Brain Extracts Brains from male Sprague-Dawley rats were rapidly removed following sacrifice. Whole brains with cerebellum removed were homogenized in 100 volumes of Tris-HCl buffer (pH 7.4 at 25°). Tissue homogenates were washed twice in the same buffer by centrifugation at 48,000 g for 10 min. Pellets were resuspended in the same buffer.

Displacement of delta-type opiate receptor ligands was determined by incubating 100μl of the above-described brain homogenate (5% original wet w/v) with 1 nM of [³H][p-Cl-Phe⁴]DPDPE (40 Ci/mM, New England Nuclear Inc.) and varying concentrations of compounds in Table I and II at 25° C. [³H][p-Cl-Phe⁴]DPDPE, commercially available, is highly selective for delta-type receptors. Total incubation volume was 2 ml. After 40 min., the mixture was rapidly filtered through Whatman GF/B glass fiber filters and washed 3 times with 5 ml of ice-cold buffer.

To examine the ability of each analog to displace mu-type receptor ligands, similar reactions with minor modifications, were set up, except [³H]CTOP (30 Ci/mmol, New England Nuclear Inc.), a highly mu-selective peptide analog of somatostatin, was used in place of [³H][p-Cl-Phe⁴]DPDPE.

Filter-bound radioactivity was quantitated by liquid scintillation spectrophotometry with an efficiency of 46%. Radio-ligand displaced by 1 μM natrexone hydrochloride was defined as specific tissue binding.

We claim:

1. A polypeptide of the formula:

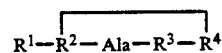

wherein
R¹ is L-tyrosine, or L-tyrosine with a halogen or methyl substitutions;
R² is D-penicillamine or D-cysteine;
R³ is phenylalanine or phenylalanine with one to three same or different halogen, nitro, or methyl substitutions; and
R⁴ is D-penicillamine, L-penicillamine, D-cysteine or L-cysteine.

2. A polypeptide as claimed in claim 1 wherein R¹ is L-tyrosine.

3. A polypeptide as claimed in claim 1 wherein R² and R⁴ are D-penicillamine.

4. A polypeptide of the formula:

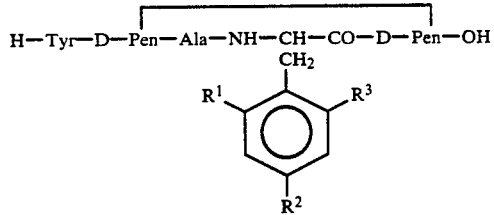

wherein R¹, R², and R³ are the same or different and are H, F, Cl, Br, I, NO₂, NH₂, or a lower alkyl of less than five carbons.

5. A polypeptide as claimed in claim 4 wherein R¹, R², and R³ are all hydrogen.

6. A polypeptide as claimed in claim 4 wherein R¹ and R³ are H, and R² is F.

7. A polypeptide as claimed in claim 4 wherein R¹ and R³ are H, and R² is Cl.

8. A polypeptide as claimed in claim 4 wherein R¹ and R³ are H, and R² is Br.

9. A polypeptide as claimed in claim 4 wherein R¹ and R³ are H, and R² is I.

10. A polypeptide as claimed in claim 4 wherein R¹ and R³ are H, and R² is NO₂.

11. A pharmaceutical composition comprising an opioid receptor agonist having enhanced specificity for the delta opioid receptors, the agonist having the formula:

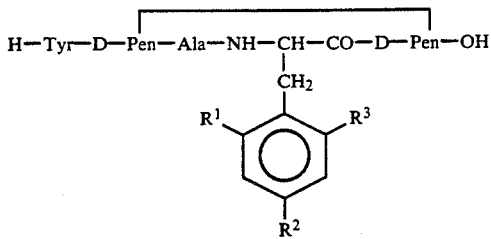

wherein $R^1$, $R^2$, and $R^3$ are the same or different and are H, F, Cl, Br, I, $NO_2$, $NH_2$ or a lower alkyl of less than five carbons; or a pharmaceutically acceptable salt thereof, in a pharmaceutically acceptable carrier.

12. A pharmaceutical composition as claimed in claim 11 wherein $R^1$, $R^2$ and $R^3$ are all H.

13. A pharmaceutical composition as claimed in claim 11 wherein $R^1$ and $R^3$ are H, and $R^2$ is F.

14. A pharmaceutical composition as claimed in claim 11 wherein $R^1$ and $R^3$ are H, and $R^2$ is Cl.

15. A pharmaceutical composition as claimed in claim 11 wherein $R^1$ and $R^3$ are H, and $R^2$ is Br.

16. A pharmaceutical composition as claimed in claim 11 wherein $R^1$ and $R^3$ are H, and $R^2$ is I.

17. A Pharmaceutical composition as claimed in claim 11 wherein $R^1$ and $R^3$ are H, and $R^2$ is $NO_2$.

* * * * *

UNITED STATES PATENT AND TRADEMARK OFFICE
CERTIFICATE OF CORRECTION

PATENT NO. : 5,326,751
DATED : July 5, 1994
INVENTOR(S) : Ronald C. Haaseth
  Victor J. Hruby It is certified that error appears in the above-identified patent and that said Letters Patent is hereby corrected as shown below:

In Column 1, line 4, after the title, insert the following text:

This invention was made with United States Government support awarded by the National Institute of Drug Abuse, Grant Nos. NS 19972 and P01 DA 06284. The United States Government has certain rights in this invention.--

Signed and Sealed this

Thirty-first Day of January, 1995

Attest:

BRUCE LEHMAN

Attesting Officer

Commissioner of Patents and Trademarks